United States Patent [19]

Tomlin et al.

[11] 3,965,109
[45] June 22, 1976

[54] CERTAIN ARYL AMINO PYRIDINES

[75] Inventors: Clive Dudley Spencer Tomlin, Maidenhead; Charles Brian Barlow, Camberley; Brian Graham White, Crowthorne, all of England

[73] Assignee: Imperial Chemical Industries Limited, London, England

[22] Filed: Sept. 16, 1975

[21] Appl. No.: 613,955

Related U.S. Application Data

[62] Division of Ser. No. 230,514, Feb. 29, 1972, Pat. No. 3,926,611.

[30] Foreign Application Priority Data

Mar. 19, 1971 United Kingdom................ 7291/71

[52] U.S. Cl.......................... 260/294.9; 260/296 R; 71/94; 424/263
[51] Int. Cl.$^2$........................................ C07D 213/57
[58] Field of Search..................... 260/296 R, 294.9

[56] References Cited

UNITED STATES PATENTS 3,930,007   12/1975   Barlow et al........................ 424/263

Primary Examiner—Alan L. Rotman
Attorney, Agent, or Firm—Cushman, Darby & Cushman

[57] ABSTRACT

The present invention relates to polysubstituted aryl amino pyridines herbicidal and pesticidal compositions useful, inter alia, in controlling pests including fungal infections of plants, and in inhibiting the growth of unwanted vegetation; to chemical compounds useful as active ingredients of such compositions; to methods of controlling pests including fungal infections of plants: and to methods of inhibiting the growth of unwanted vegetation.

4 Claims, No Drawings

CERTAIN ARYL AMINO PYRIDINES

This is a division of application Ser. No. 230,514 filed Feb. 29, 1972, now U.S. Pat. 3,926,611.

According to the present invention there is provided a herbicidal and pesticidal composition comprising as an active ingredient an arylaminopyridine of the formula:

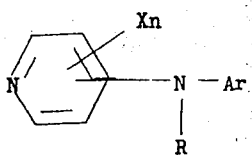

or a salt thereof, wherein R represents a hydrogen atom, an acyl radical, or a hydrocarbyl radical; Ar represents an aryl radical optionally substituted by one or more chlorine, bromine, fluorine nitro, cyano, perhalocarbyl sulphamoyl, hydrocarbyl, hydrocarbyloxy, or hydrocarbylthio radicals; X represents a chlorine, bromine, fluorine, nitro, cyano, hydrocarbyloxy or hydrocarbylthio radical; and $n$ is 3 or 4; in admixture with a solid diluent or a liquid diluent containing a surface-active agent. Preferred hydrocarbyl radicals are alkyl groups of 1 to 4 carbon atoms. Examples of preferred perhalocarbyl radicals include the trifluoromethyl radical. Examples of preferred hydrocarbyloxy groups include alkoxy radicals of 1 to 4 carbon atoms. Examples of preferred hydrocarbylthio radicals include alkylthio radicals of 1 to 4 carbon atoms.

Preferred compounds as active ingredients are those in which the aryl radical is a substituted phenyl or naphthyl radical.

Preferably the bond between the pyridine ring and the group

in the foregoing formula is located at the 4-position of the pyridine ring. Particularly preferred compounds as active ingredients are those in which the group R represents a hydrogen atom. Preferred compounds for use as active ingredients include those in which each group X is a fluorine or chlorine atom and $n$ is 4. Where the group R represents an acyl group, the acyl group may for example be derived from a carboxylic acid; for example it may be an alkanoyl group of from 2 to 5 carbon atoms. The acyl group may also be a carbamoyl group, for example a carbamoyl group bearing one or two alkyl substituents each of 1 to 4 carbon atoms. Where R represents a hydrocarbyl group, it may be for example an alkyl group of from 1 to 5 carbon atoms. Preferably the aryl group Ar bears a nitro, cyano or trifluoromethyl substituent. The term salt is intended to include both salts formed from reaction of the compounds of the foregoing formula with bases, for example salts formed from metal cations and ammonium cations, and salts formed by reaction of compounds of the foregoing formula with acids.

Particular examples of compounds useful as active ingredients of the compositions of the invention are listed in Table I below.

TABLE I

| Compound No. | Structural Formula | Melting point °C |
|---|---|---|
| 1 | (2,6-difluoro-3,5-dichloropyridin-4-yl)-NH-(2,4-dinitrophenyl) | 116 |
| 2 | (2,6-difluoro-3,5-dichloropyridin-4-yl)-NH-phenyl | 77 |
| 3 | (2,6-difluoro-3,5-dichloropyridin-4-yl)-NH-(2,6-dichlorophenyl) | 106 |

Table I
continued

| Compound No. | Structural Formula | Melting point °C. |
|---|---|---|
| 4 | 2,6-difluoro-3,5-dichloro-4-pyridyl-NH-(4-fluorophenyl) | 107 |
| 5 | 2,6-difluoro-3,5-dichloro-4-pyridyl-NH-(2-trifluoromethyl-4-nitrophenyl) | 117 |
| 6 | 2,6-difluoro-3,5-dichloro-4-pyridyl-NH-(2,4-dinitro-5-fluorophenyl) | 185 |
| 7 | 2,6-difluoro-3,5-dichloro-4-pyridyl-NH-(2,4,6-trichlorophenyl) | 131 |
| 8 | 2,3,5,6-tetrachloro-4-pyridyl-NH-(2,4-dinitrophenyl) | 196 |
| 9 | 2,6-difluoro-3,5-dichloro-4-pyridyl-NH-(pentachlorophenyl) | 125 |
| 10 | 2,6-difluoro-3,5-dichloro-4-pyridyl-NH-(pentafluorophenyl) | 59 |

Table I
continued

| Compound No. | Structural Formula | Melting point °C. |
|---|---|---|
| 11 | 2,6-difluoro-3,5-dichloro-4-(2-nitroanilino)pyridine | 126 |
| 12 | 2,6-difluoro-3,5-dichloro-4-(2,3,5,6-tetrafluoro-4-nitroanilino)pyridine | 123 |
| 13 | 2,6-difluoro-3,5-dichloro-4-(2-bromo-5-trifluoromethylanilino)pyridine | 74 |
| 14 | 2,6-difluoro-3,5-dichloro-4-(4-nitroanilino)pyridine | 170 |
| 15 | 2,3,5,6-tetrafluoro-4-(2,4-dinitroanilino)pyridine | 118 |
| 16 | 2,6-difluoro-3,5-dichloro-4-(2-nitro-4-trifluoromethylanilino)pyridine | 113 |
| 17 | 2,6-difluoro-3,5-dichloro-4-(3-trifluoromethylanilino)pyridine | 71 |

Table I
continued

| Compound No. | Structural Formula | Melting point °C. |
|---|---|---|
| 18 | 2,6-difluoro-3,5-dichloro-4-pyridyl-NH-(2-nitro-4-methoxyphenyl) | 136 |
| 19 | 2,6-difluoro-3,5-dichloro-4-pyridyl-NH-(2,3,5,6-tetrafluoro-4-cyanophenyl) | 160 |
| 20 | 2,6-difluoro-3,5-dichloro-4-pyridyl-NH-(heptafluoronaphthyl) (1 or 2 isomer) | 135-137 |
| 21 | 2-fluoro-3-chloro-5-chloro-6-methoxy-4-pyridyl-NH-(2,3,5,6-tetrafluoro-4-cyanophenyl) | 130-131 |
| 22 | 2,6-difluoro-3,5-dichloro-4-pyridyl-NH-(2,4,6-trinitrophenyl) | 147 |
| 24 | 2,6-difluoro-3,5-dichloro-4-pyridyl-NH-(2,5-dichloro-4-nitrophenyl) | 143 |
| 25 | 2,6-difluoro-3,5-dichloro-4-pyridyl-NH-(2-nitro-4-nitronaphthyl) | 182 |

Table I continued

| Compound No. | Structural Formula | Melting point °C |
|---|---|---|
| 26 | 2,6-difluoro-3,5-dichloro-4-[(2-cyano-4-nitrophenyl)amino]pyridine | 236-237 |
| 27 | 2,6-difluoro-3,5-dichloro-4-[(2,6-dichloro-4-nitrophenyl)amino]pyridine | 171.6-172.6 |
| 28 | 2,3,5,6-tetrafluoro-4-[(2-trifluoromethyl-4-nitrophenyl)amino]pyridine | 107.7-108 |
| 29 | 2,6-difluoro-3,5-dichloro-4-[(2,6-dinitro-4-chlorophenyl)amino]pyridine | 167.5-167.7 |
| 30 | 2,6-difluoro-3,5-dichloro-4-[(2,3,5,6-tetrafluoro-4-bromophenyl)amino]pyridine | 137.9-139.2 |
| 31 | 2,6-difluoro-3,5-dichloro-4-[(2,6-dichloro-4-(N,N-dimethylsulfamoyl)phenyl)amino]pyridine | 191-192.4 |
| 32 | 2,6-difluoro-3,5-dichloro-4-[(2-trifluoromethyl-4-nitrophenyl)amino]pyridine | 94.7-95.2 |

Table I
continued
| Compound No. | Structural Formula | Melting point °C |
|---|---|---|
| 33 | 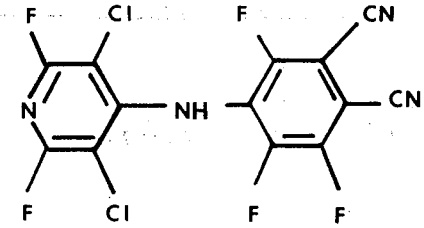 | 166·5–167·2 |
| 34 | 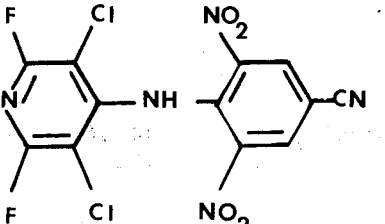 | 166·6–167·6 |
| 35 | 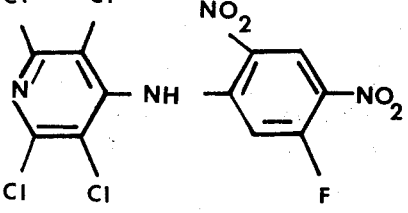 | 233·2–234·2 |
| 36 | 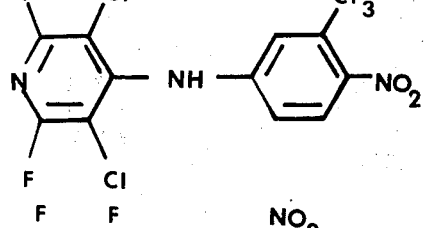 | 133·2–133·7 |
| 37 | 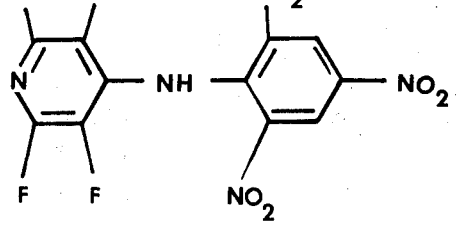 | 168·2–169·2 |
| 38 | 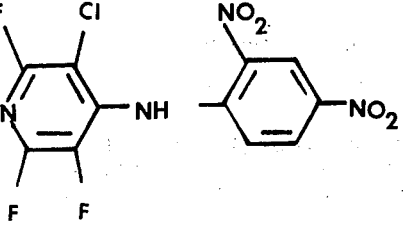 | 121·6–122·6 |
| 39 | 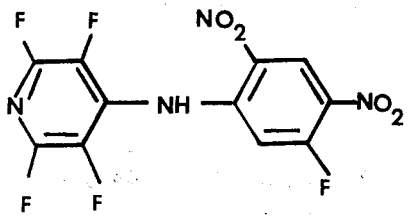 | 115·9–116·4 |

Table I continued
| Compound No. | Structural Formula | Melting point °C. |
|---|---|---|
| 40 | 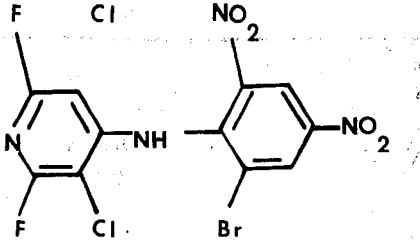 | 168·6–168·9 |
| 41 | 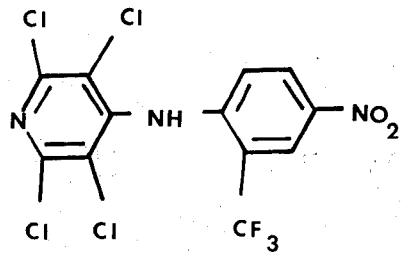 (or 2 isomer) | 170·7–171·2 |
| 42 | 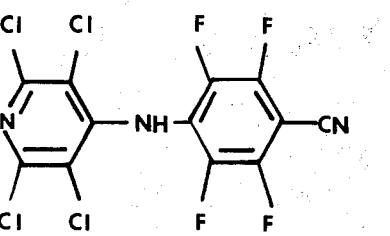 | 161·2–162·7 |
| 43 | 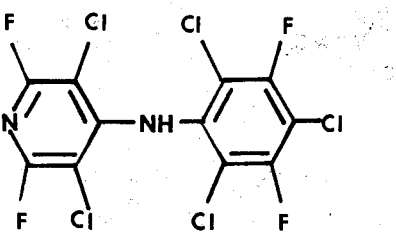 | 108·2–108·8 |
| 44 | 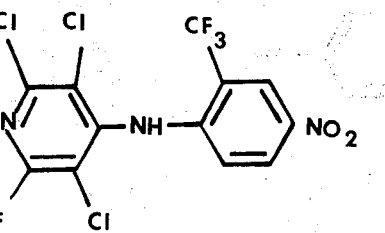 | 116·0–116·6 |
| 45 | 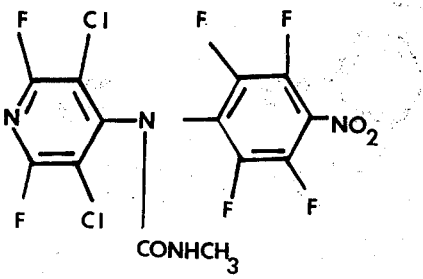 | 183·2–185·5 |

TABLE I
-continued
| Compound No. | Structural Formula | Melting point °C |
|---|---|---|
| 46 | 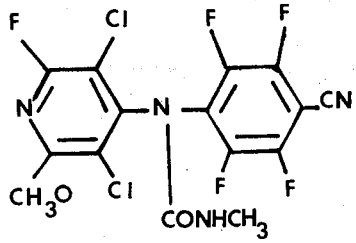 | 205·5 207·6 |
| 47 | 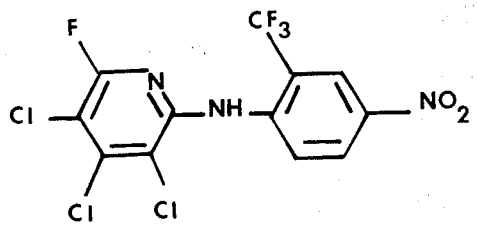 | 126·5– 127·7 |
| 48 | 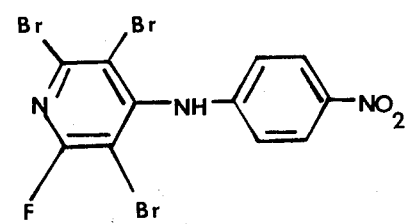 | 118– 119.7 |
| 49 | 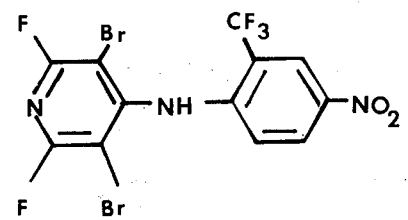 | 114·5– 115.7 |
| 50 | 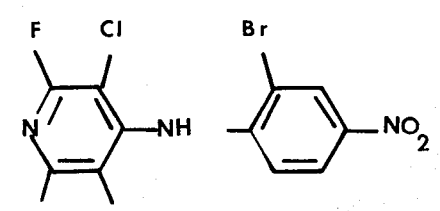 | 155.3– 156.6 |
| 51 | 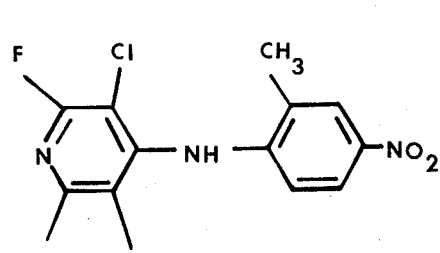 | 165– 166.6 |

The formulae given in Table I above are believed to be those which correspond most closely to the molecular structure of the compounds. However, a compound of the formula:

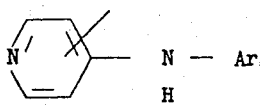

is, in principle, capable of existing in different tautomeric forms such, as for example the following:

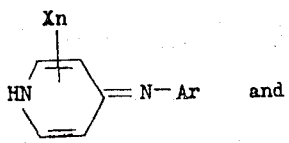 and 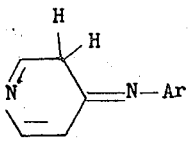

The formulae given in Table I above are to be considered as representative of and including all such tautomeric forms.

Compositions according to the invention may be in the form of dusting powders or granules wherein the active ingredient is mixed with a solid diluent or carrier. Suitable solid diluents or carriers may be, for example kaolinite (china clay), montmorillonite, attapulgite, talc, pumice, silica, calcium carbonate, gypsum, powdered magnesia, Fuller's earth, and diatomaceous earth. Compositions for dressing seed, for example, may comprise an agent assisting the adhesion of the composition of the seed, for example a mineral oil.

The composition may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic, or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyland triisopropylnaphthalene sulphonic acids.

Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, the lecithins, and block copolymers of ethylene oxide and propylene oxide.

Suitable suspending agents are, for example bentonite, pyrogenic silica, and hydrophilic colloids, for example polyvinylpyrrolidone and sodium carboxymethylcellulose, and the vegetable gums, for example gum acacia and gum tragacanth.

The aqueous solutions dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, xylenes and trichloroethylene. Concentrated solutions of the active ingredient in an organic solvent containing a dispersing agent to facilitate the dispersion of the organic solvent to form an emulsion when mixed with water are known as "emulsifiable concentrates."

The compounds of the invention may also be formulated into compositions comprising capsules or microcapsules containing either the active ingredient itself, or a composition containing the active ingredient, and prepared by any of the known encapsulation or microencapsulation techniques.

The compositions to be used as sprays may also be in the form of aerosols wherein the formulation is held in a container under pressure in the presence of a propellant such as fluorotrichloromethane or dichlorodifluoromethane.

The compositions which are to be used in the form of aqueous dispersions or emulsions are generally supplied in the form of a concentrate contaning a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10 – 85% by weight of the active ingredient or ingredients and generally from 25 – 60% by weight of the active ingredient or ingredients. When diluted to form aqueous preparations, such preparations may contain varying amounts of the active ingredient or ingredients depending upon the purpose for which they are to be used, but an aqueous preparation containing between 0.0001% and 1.0% by weight of the active ingredient or ingredients may be used.

The arylaminopyridine derivatives specified hereinbefore as active ingredients of the compositions of the invention are toxic towards a wide variety of pests, including the following:

| | |
|---|---|
| *Tetranychus telarius* | (red spider mites) |
| *Aphis fabae* | (black aphids) |
| *Megoura viciae* | (green aphids) |
| *Aedes aegypti* | (mosquitos) |
| *Musca domestica* | (houseflies) |
| *Pieris brassicae* | (cabbage white caterpillars) |
| *Plutella maculipennis* | (diamond backed moth caterpillars) |
| *Phaedon cochleariae* | (mustard beetles) |
| *Meloidogyne incognita* | (nematodes) |
| *Agriolimax reticulatus* | (grey field slugs) |
| *Calandra granaria* | (grain weevils) |

The term pests is intended to include fungal pathogens of plants and seeds including for example, the following:

| | |
|---|---|
| Puccinia recondita | (brown rust on wheat) |
| Phytophthora infestans | (late blight on tomatoes) |
| Plasmopara viticola | (downy mildew on vines) |
| Uncinula necator | (powdery mildew on vines) |
| Piricularia oryzae | (blast on rice) |
| Podosphaera leucotricha | (powdery mildew on apples) |
| Venturia inaequalis | (apple scab) |

Certain of the compounds show algicidal properties.

The arylaminopyridine compounds are also toxic towards bacteria which cause bacterial diseases of plants, for example the following:

| Bacterium | Common name |
|---|---|
| Agrobacterium tumifaciens | Crown gall of vegetables |
| Corynebacterium michiganense | Canker of tomatoes |
| Xanthomonas malvacearum | Blackarm of cotton |
| Erwinia carotovora | Soft rot of vegetables |
| Xanthomonas oryzae | Rice blight |
| Pseudomonas syringae | Dieback of beans, stone fruit |
| Streptomyces scabies | Potato scab |
| Pseudomonas mors prunum | Canker of stone fruit |
| Pseudomonas phaseolicola | Halo blight of beans |
| Erwinia amylovora | Fire blight of pear and apple |

The arylaminopyridine compounds are also toxic towards post harvest saprophytic fungi, for example the following:

| Fungus | Host Crop | Name |
|---|---|---|
| Botrytis tulipae | Bulbs | Fire |
| Nigrospora sphaerica | Bananas | Squirter |
| Phomopsis citri | Citrus | Scab |
| Alternaria citri | Citrus | Stem end rot |
| Pencillium digitatum | Citrus | Green mould |
| Gloeosporium musarum | Bananas | Blackend |
| Fusarium caeruleum | Potato | Dry rot |
| Ceratocystis paradoxa | Sugar cane, pineapple | Pineapple disease |
| Phoma exigua | Potato | Gangrene |
| Phytophthora citrophthora | Citrus | Grey mould |
| Botryodiplodia theobromae | Bananas | Black end |
| Diplodia natalensis | Citrus | Stem end rot |

The compositions of the invention, or the arylaminopyridine compounds used as the active ingredients of the compositions, may be used to combat pests in a variety of ways. Thus the pests themselves, or the locus of the pests or the pest habitat may be treated to control the pests. Accordingly, in a further apsect the invention provides a method of combating pests, which comprises applying to the pests, the locus of the pests, or the habitat of the pests an arylaminopyridine compound of the formula:

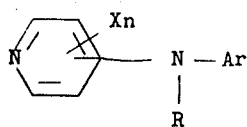

wherein X, R, Ar and n are as hereinfore defined, or a composition according to the invention.

In a further aspect, the invention provides a method of treating plants to render them less susceptible to damage by pests, which comprises applying to the plants, or to the seeds, corms, bulbs, tubers, rhizomes, or other propagative parts of the plants, a non-phytotoxic but pesticidally effective amount of an arylaminopyridine of the formula:

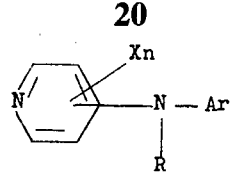

or a salt thereof, wherein X, Ar, R and n are as hereinbefore defined.

The invention additionally provides a method of inhibiting the growth of unwanted vegetation, which comprises applying to the vegetation, or to the locus of the vegetation or of seeds thereof, a herbicidally effective amount of an arylaminopyridine compound of the formula:

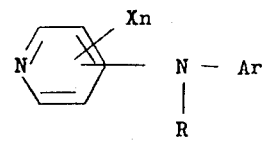

wherein X, Ar, R and n are as hereinbefore defined. The amount of arylaminopyridine compound used to inhibit the growth of vegetation will depend upon the particular compound chosen as well as on the identity of the vegetation, but in general an amount of from 0.22 to 11.2 kilograms per hectare (0.2 to 10 pounds per acre) is suitable.

In another aspect the invention provides arylaminopyridines of the formula:

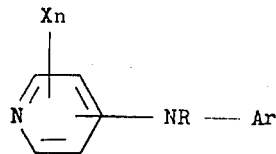

wherein R represents a hydrogen atom, an acyl radical, or a hydrocarbyl radical; Ar represents an aryl radical optionally substituted by one or more chlorine, bromine, fluorine, nitro, cyano, perhalocarbyl, sulphamoyl, hydrocarbyl, hydrocarbyloxy, or hydrocarbylthio radicals; X represents a chlorine, bromine, fluorine, nitro, cyano, hydrocarbyloxy, or hydrocarbylthio radical, and n is 3 or 4, provided that when X is Cl and n is 4, the aryl radical contains at least two substituents.

Preferred compounds according to the invention are those of the formula above wherein Ar is a substituted phenyl or naphthyl radical. Especially preferred compounds are those in which the group

is linked to the 4 position of the pyridine ring. Further preferred compounds are those in which R is a hydrogen atom. Particularly preferred compounds are those in which each group X represents a fluorine or chlorine atom and n is 4.

The arylaminopyridine compounds of the last foregoing formula may conveniently be prepared by a process wherein an aminopyridine is reacted with a base and with an aryl halide Ar Hal according to the following reaction scheme;

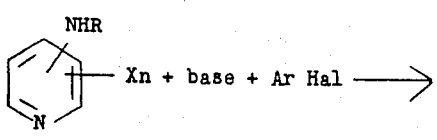 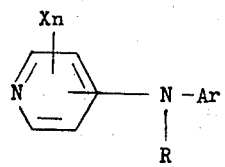

Alternatively an arylamino compound ArNHR may be reacted with a base and with a halogenopyridine according to the following reaction scheme:

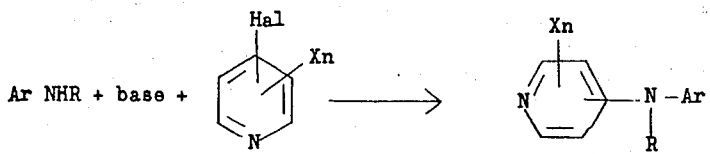

In the above reaction shcemes, the symbol Hal stands for halogen, while the symbols X, R, Ar and $n$ have the meanings previously assigned to them. An example of a base for use in the reaction is sodium hydride. Preferably the reaction is conducted in an inert diluent or solvent. Preferred solvents are aprotic dipolar solvents, for example dimethyl formamide.

Compounds having the formula:

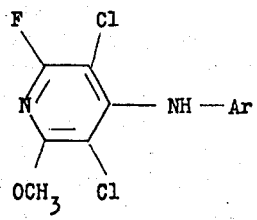

may be prepared from the intermediate

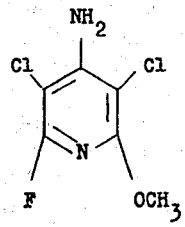

which may itself be prepared by treatment of the known compound

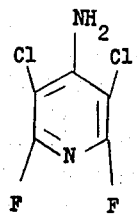

with a methanolic solution of sodium methoxide.

The following Examples illustrate the invention.

EXAMPLE 1

This Example illustrates the fungicidal properties of compounds used as active ingredients in the compositions of the invention. The compounds were tested against a wide variety of foliar fungal diseases of plants. In the test, a composition comprising an aqueous solution or suspension of the test compound was sprayed on to the foliage or uninfected plants; the soil in which the plants were growing was also drenched with the composition. The compositions used for spraying and drencing contained 100 parts per million (ppm.) of the test compound except where otherwise stated in the table of results below. After spraying and drenching, the plants were then exposed to infection with the diseases it was desired to control, along with control plants not treated with the compound. After a period of days, depending upon the particular disease, the extent of the disease was visually assessed, as a percentage of the disease established upon the control plants which had not been treated with the compound under test, according to the grading scheme below

| Grading | Amount of disease as a percentage of disease on control plants |
|---|---|
| 0 | 61 to 100 |
| 1 | 26 to 60 |
| 2 | 6 to 25 |
| 3 | 0 to 5 |

In Table 2 below the names of the disease is given in the first column, and in the second column is given the time which elapsed between exposing the plants to infection and assessing the amount of disease. Table 3 gives the test results.

TABLE 2

| Disease and Plant | Time interval (days) | Disease code letter |
|---|---|---|
| Puccinia recondita (wheat) | 10 | A |
| Phytophthora infestans (tomato) | 3 | B |
| Plasmopara viticola (vine) | 10 | C |
| Uncinula necator (vine) | 10 | D |
| Piricularia oryzae (rice) | 7 | E |
| Podosphaera leucotricha (apple) | 7 | F |
| Venturia inaequalis (apple) | 21 | G |
| Botrytis cinerea (chocolate spot of beans | 3 | H |

TABLE 3

| Compound No. (Table 1) | Disease code letter (Table 2) | | | | | | | |
|---|---|---|---|---|---|---|---|---|
| | A | B | C | D | E | F | G | H |
| *3 | 0 | 0 | 2 | 3 | 0 | 2 | 0 | — |
| 5 | 3 | — | 3 | 3 | 0 | 3 | 3 | — |
| *6 | 0 | 3 | 3 | 2 | 3 | — | — | 3 |
| 7 | 2 | 0 | 0 | 0 | 0 | — | — | 0 |
| *8 | 0 | 3 | 3 | 0 | 0 | — | — | — |
| 9 | 3 | 0 | 0 | 3 | 3 | — | — | 2 |
| 12 | 2 | — | 3 | 3 | 0 | 3 | — | 3 |
| 13 | 0 | — | 3 | 0 | 2 | 0 | — | 2 |
| 15 | 2 | — | 3 | 3 | — | 3 | — | — |
| 16 | 0 | 0 | 3 | 0 | 0 | 2 | — | 0 |
| 17 | 0 | 1 | 3 | 0 | 0 | — | — | 3 |
| 19 | — | — | — | — | — | — | 3 | — |
| 20 | 3 | — | 3 | — | 2 | 3 | — | 1 |
| 21 | 3 | — | 3 | — | 3 | 3 | 3 | 2 |

A dash (—) means that no test was performed
*These compounds were applied at a rate of 50 ppm. spray combined with a 200 ppm soil drench.

Table 4 below gives the results of tests with some further compounds listed in Table 1.

TABLE 4

| Compound No. (Table 1) | Disease code letter (Table 2) | | | | | | | |
|---|---|---|---|---|---|---|---|---|
| | A | B | C | D | E | F | G* | H |
| 24 | 0 | 3 | 3 | 3 | 0 | — | — | 3 |
| 25 | 2 | 3 | 3 | 3 | 0 | — | 0 | 0 |
| 26 | P | 3 | 3 | P | 0 | 3 | 3 | 1 |
| 27 | 0 | P | 3 | 3 | P | 3 | 3 | 3 |
| 28 | 0 | P | 3 | 3 | P | 3 | 3 | P |
| 29 | P | P | 3 | 3 | P | 3 | 3 | 3 |
| 30 | 0 | 1 | 3 | 0 | 0 | 3 | — | 0 |
| 31 | 2 | 0 | 3 | 3 | 0 | 3 | — | 0 |
| 32 | 3 | P | 3 | 3 | P | 3 | — | P |
| 33 | 2 | 3 | 3 | 2 | 3 | 3 | — | 0 |
| 34 | P | 3 | 3 | 3 | P | 3 | — | P |
| 35 | 2 | 3 | 3 | 0 | 2 | 0 | 0 | 2 |
| 36 | 2 | 2 | 3 | 0 | 1 | 2 | 0 | 0 |
| 37 | 0 | 3 | 3 | P | 0 | P | — | 2 |
| 38 | 1 | P | 3 | 3 | 2 | 3 | 3 | 2 |
| 39 | 1 | 2 | 3 | 0 | 1 | 0 | 3 | 3 |
| 40 | 0 | P | 3 | 3 | 1 | 3 | 2 | 3 |
| 41 | 0 | P | 3 | 3 | P | 3 | 3 | 3 |
| 42 | 3 | P | P | P | 0 | 3 | — | 3 |
| 43 | P | P | — | 3 | P | 3 | — | P |
| 44 | 2 | P | 3 | 3 | 0 | 3 | — | P |

The symbol P means that the compound was too phytotoxic for an assessment of disease control to be made.
*For the test on apple scab (G) a concentration of 25 ppm was used.

EXAMPLE 2

This Example illustrates the algicidal activity of compounds used as active ingredients of compositions according to the invention. In a test for algicidal activity, a mixed culture of green algae in water (1 ml.) was made up to 5 ml. in a glass tube with an aqueous suspension or solution of the compound under test containing sufficient compound to bring the concentration to 20 parts per million of test compound, together with nutrients to support the growth of the algae. After 1 week the intensity of "greening" in the glass tubes was compared with untreated control cultures of algae, and the amount of algal growth assessed on a scale of 0 to 3, according to the grading scheme below:

| Grading | Algal growth as % of untreated control |
|---|---|
| 0 | 61 to 100 |
| 1 | 25 to 60 |
| 2 | 6 to 25 |
| 3 | 0 to 5 |

The results of the test are given in Table 5 below.

TABLE 5

| Compound No. (see Table 1) | Grading |
|---|---|
| 4 | 3 |
| 5 | 3 |
| 6 | 3 |
| 9 | 2 |
| 10 | 3 |
| 12 | 3 |
| 14 | 3 |
| 17 | 2 |
| 19 | 2 |

EXAMPLE 3

This Example illustrates the activity of compounds used as active ingredients in compositions according to the invention as toxicants for a variety of insect and other pests. The compounds were used in the form of a liquid preparation containing 0.1% by weight of the compound, except in the tests with Aedes aegypti and Meloidogyne incognita, where the preparations contained 0.01% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name LISSAPOL NX until the liquid preparations contained the required concentration of the compound. LISSAPOL is a registered Trade Mark.

The test procedure adopted with regard to each pest was basically the same and comprised supporting a number of the pests on a medium which was usually a host plant or a foodstuff on which the pests feed and treating either or both the pests and the medium with the preparations.

The mortality of the pests was then assessed at periods usually varying from one to three days after the treatment.

The results of the tests are given below in Table 6. In this table the first column indicates the name of the pest species. The subsequent columns indicate the host plant or medium on which it was supported, the number of days which were allowed to elapse after the treatment before assessing the mortality of the pests, and the results obtained for each of the compounds, numbered as in Table 1 above. The assessment is expressed in integers which range from 0 to 3.

O represents less than 30% kill
1 represents 30 – 49% kill
2 represents 60 – 90% kill
3 represents over 90% kill
C indicates a chemosterilant effect.
A indicates an antifeeding effect.

A dash (-) in Table 6 indicates that no test was carried out.

TABLE 6

| Pest Species | Support medium | No. of days | \multicolumn{19}{c}{No. of Compound (Table 1)} |
|---|---|---|---|---|---|---|---|---|---|---|---|---|---|---|---|---|---|---|---|---|
| | | | 1 | 2 | 3 | 4 | 5 | 8 | 9 | 10 | 11 | 12 | 13 | 15 | 16 | 18 | 19 | 20 | 21 | 22 |
| Tetranychus telarius (red spider mites, adults) | French Bean | 3 | 3 | 3 | 0 | 0 C | 3 | 3 | 3 | 3 | 0 | 3 | 0 | 3 | 2 C | 0 | 3 | 3 | 3 | 0 |
| Tetranychus telarius (red spider mites, eggs) | French Bean | 3 | 0 | 0 | 2 | 0 | 3 | 3 | — | — | 0 | 3 | 0 | 2 | 0 | 2 | 3 | 3 | 3 | 0 |
| Aphis fabae (green aphids) | Broad Bean | 2 | 3 | 0 | 0 | 0 | 3 | 0 | 0 | 0 | 0 | 3 | 0 | 0 | 0 | 0 | 3 | 2 | 3 | 0 |
| Megoura viceae (black aphids) | Broad Bean | 2 | 3 | 0 | 0 | 0 | 3 | 0 | 0 | 0 | 0 | 3 | 0 | 0 | 0 | 0 | 3 | 2 | 3 | 0 |
| Aedes aegypti (mosquito larvae) | Water | 1 | 0 | 0 | 0 | 0 | 0 | 0 | 3 | 2 | 0 | 3 | 0 | 0 | 0 | 0 | 3 | 1 | 0 | 3 |
| Aedes aegypti (mosquito adults) | Plywood | 1 | 2 | 0 | 0 | 0 | 0 | 0 | 0 | 2 | 0 | 0 | 0 | 0 | 0 | 0 | 3 | 0 | 0 | 0 |
| Musca domestica (houseflies - contact test*) | Milk/ Sugar | 2 | 0 | 0 | 0 | 0 | 0 | 0 | 3 | 0 | 0 | 2 | 0 | 2 | 0 | — | 3 | 0 | 0 | 2 |
| Pieris brassicae (cabbage white caterpillars) | Cabbage | 2 | — | 0 | 0 | 0 A | 3 A | 0 | 0 | 0 | 0 | 0 | 0 A | 3 A | 0 | 0 | 2 A | 0 | 0 A | 0 A |
| Plutella maculipennis (diamond back moth larvae) | Mustard/ paper | 2 | 0 | 0 A | 0 | 0 | 1 A | 0 A | 3 A | 0 | 0 | 0 | 0 A | 0 A | 0 | 0 | 0 | 3 | 0 | 1 A |
| Phaedon cochleariae (mustard beetles) | Mustard/ paper | 2 | 0 | 0 | 0 | 0 | 0 | 0 A | 1 A | 0 | 0 | 0 | 0 A | 2 A | 0 | 0 | 0 | 0 | 0 | 0 |
| Meloidogyne incognita (nematodes) | Water | 1 | — | — | 2 | 2 | — | — | — | — | 2 | — | 0 | — | 2 | 0 | — | — | 2 | — |

*In the contact test the flies are sprayed directly; in the residual test the flies are placed on a medium that has previously been treated.

Compounds Nos. 1, 4, 5, 7, 8, 9, 10 and 13 gave rise to abnormal growth effects in the larva of mosquitos (*Ades aegypti*)

Table 7 below gives the results of the tests carried out on further compounds listed in Table 1.

EXAMPLE 4

This Example illustrates the molluscicidal activity of compounds used as active ingredients in the compositions of the invention.

TABLE 7

| Pest Species | Support medium | No. of days | \multicolumn{16}{c}{No. of Compound (Table 1)} |
|---|---|---|---|---|---|---|---|---|---|---|---|---|---|---|---|---|---|---|
| | | | 24 | 25 | 27 | 28 | 29 | 30 | 32 | 33 | 34 | 38 | 40 | 41 | 42 | 43 | 44 | 46 |
| Tetranychus telarius (red spider mites, adults) | French Bean | 3 | 3 | 0 | 3 | 3 | 3 | 3 | 3 | 3 | 3 | 3 | 3 | 3 | 3 | 3 | 3 | 2 |
| Tetranychus telarius (red spider mites, eggs) | French Bean | 3 | 0 | 2 | 3 | 3 | — | 0 | 3 | 3 | 3 | 3 | 3 | 3 | 3 | 3 | 3 | 0 |
| Aphis fabae (green aphids) | Broad bean | 2 | 0 | 0 | 3 | 3 | 3 | 0 | 3 | 0 | 3 | 0 | 3 | 0 | 3 | 3 | 0 | 0 |
| Megoura viceae (black aphids) | Broad Bean | 2 | 0 | 0 | 3 | 3 | 3 | 0 | 0 | 0 | 0 | 0 | 3 | 0 | 3 | 3 | 0 | 0 |
| Aedes aegypti (mosquito larvae) | Water | 1 | 3 | 3 | 3 | 3 | 3 | 3 | 3 | 0 | 3 | 3 | 3 | 3 | 3 | 3 | 3 | 3 |
| Aedes aegypti (mosquito adults) | Plywood | 1 | 0 | 0 | 2 | 3 | 0 | 2 | 2 | 2 | 0 | 0 | 0 | 0 | 0 | 0 | 0 | 0 |
| Musca domestica (houseflies, contact test*) | Milk/ sugar | 2 | 1 | 0 | 3 | 3 | 0 | 0 | — | — | — | 0 | 3 | 2 | 3 | 3 | 3 | 0 |
| Pieris brassicae (cabbage white caterpillars) | Cabbage | 2 | 0 | 3 | 0 | 3 | 0 | 3 | 3 | 3 | 0 | 3 | 0 | 0 | 3 | 3 | 3 | 0 |
| Plutella maculipennis (diamond back moth larvae) | Mustard/ paper | 2 | 0 | 0 | 0 | 3 | 0 | 1 | 2 | 1 | 2 | 0 | 0 | 1 | 0 | 2 | 0 | 0 |
| Phaedon cochleariae (mustard beetles) | Mustard/ paper | 2 | 0 | 2 | 0 | 3 | 0 | 0 | 0 | 0 | 0 | 0 | 2 | 2 | 0 | 0 | 0 | 0 |
| Meloidogyne incognita (nematodes) | Water | 1 | 0 | 3 | — | — | 0 | 3 | — | 0 | — | — | — | — | — | — | — | — |

*In the contact test the flies were sprayed with the solution of the compound under test.

In tests similar to those set forth in the above table, compounds 27, 28, 32, 34 40 and 42 each killed 60 to 100% of German cockroaches (*Blattella germanica*); compounds 28 and 42 each killed 60 to 100% of grain weevils (*Calandra granaria*); and compounds 27, 28, 32 and 43 each killed 60 to 100% of flour beetles (*Triboleum castaneum*)

A weighed sample of the compound under test was dissolved in 0.5 c.c. of an ethanol and acetone mixture 50:50 v/v). The solution was diluted with 0.5 cc water and poured onto a calf feeding pellet in a glass Petri dish. The pellet was then air dried for 24 hours. The weight of compound used was chosen so that the dried pellet contained 4% by weight of the active ingredient. Two replicates each consisting of a plastic Petri dish containing a pellet, 2 slugs, and a moistened filter paper to maintain a high relative humidity were used in each test. The dishes were left in a cold room (10°C.) After 6 days the kill was assessed.

The slugs used were *Agriolimax reticulatus* (Mull), and they had been starved for 24 hours before the commencement of the tests. The results of the test are set out in Table 8 below.

TABLE 8

| Compound No. | % Kill of slugs |
|---|---|
| 4 | 100 |
| 8 | 100 |
| 12 | 50 |
| 15 | 50 |
| 16 | 50 |
| 18 | 50 |
| 25 | 50 |
| 27 | 100 |
| 29 | 50 |
| 30 | 100 |
| 32 | 100 |
| 34 | 100 |
| 42 | 50 |
| 43 | 100 |

EXAMPLE 5

This Example illustrates the herbicidal properties of the compounds of the present invention. The compounds were ball-milled in water containing a surface-active agent sold under the name of Lissapol and comprising a condensate of p-nonylphenol with seven to eight molar proportions of ethylene oxide. The ball-milled material was diluted with water to give a spray composition containing 0.1% of the surface-active agent, and sprayed on to young pot plants of the species listed in Table 9 below (Post-emergence test). The rate of application of the active ingredient was equivalent to 10 pounds per acre (11.2 kilograms per hectare) and the spray volume 100 gallons per acre (1123 litres per hectare). Damage to the plants was assessed on a scale of 0 to 3 where 0 represents no effect and 3 represents complete kill. In the same experiment pots of soil were sown with seeds of the plant species listed in Table 9 and then sprayed with the above spray composition at the rate of 10 pounds per acre of active ingredient (pre-emergence test). The results are given in Table 9 below.

TABLE 9

| No. of Compound (Table 1) | Pre-emergence | | | |
|---|---|---|---|---|
| | Lettuce | Tomato | Wheat | Maize |
| 5 | 3 | 3 | 2 | 0 |
| 10 | 2 | 1 | 0 | 0 |
| 12 | 3 | 3 | 3 | 3 |
| 19 | 3 | 3 | 3 | 3 |
| | Post-emergence | | | |
| 5 | 3 | 3 | 0 | 0 |

TABLE 9-continued

| 10 | 3 | 3 | 1 | 0 |
| 12 | 3 | 3 | 0 | 1 |
| 19 | 3 | 3 | 2 | 1 |

In a further test, the spray compositions prepared as described above were sprayed on to a further group of plant species, at various rates of application. In this test the damage to the plants was assessed on a scale of 0 to 5 where 0 represents no effect and 5 represents complete kill. The results are given in Table 10 below.

TABLE 10

| No. of Compound (Table 1) | Application rate, pounds/ acre | Pre- or Post emergence test | Plant Species | | | | | | | |
|---|---|---|---|---|---|---|---|---|---|---|
| | | | Sb | Ka | Ca | Pea | On | Bar | Ri | Oat |
| 5 | 1 | Pre | 0 | 0 | 2 | 0 | 0 | 5 | 3 | 2 |
| | 5 | Pre | 5 | 5 | 5 | 3 | 5 | 5 | 5 | 5 |
| | 1 | Post | 5 | 5 | 5 | 4 | 3 | 3 | 0 | 3 |
| | 5 | Post | 5 | 5 | 5 | 4 | 5 | 3 | 0 | 4 |
| 10 | 5 | Pre | 0 | 1 | 1 | 3 | 0 | 3 | — | 0 |
| | 5 | Post | 3 | 3 | 2 | 0 | 2 | 0 | 0 | 0 |
| 12 | 5 | Post | 5 | 5 | 5 | 1 | 0 | 2 | 0 | 0 |
| | 5 | Pre | 4 | 4 | 4 | 3 | — | — | — | 0 |
| 19 | 5 | Post | 2 | 3 | 0 | 0 | 1 | 2 | 2 | 0 |

An application rate of 1 pound per acre is equivalent to 1.12 kilograms per hectare, and 5 pounds per acre is equivalent to 5.6 kilograms per hectare.

The abbreviations used in Table 10 have the following meanings:

| Abbreviation | Full Name |
|---|---|
| Sb | Sugar beet |
| Ka | Kale |
| Ca | Carrot |
| On | Onion |
| Bar | Barley |
| Ri | Rice |

EXAMPLE 6

This Example illustrates the herbicidal activity of further compounds used as active ingredients in the compositions of the invention. The compounds were tested on lettuce, tomato, wheat and maize plants as described in Example 5 except that the compounds were applied at 10 kilograms per hectare in a spray volume of 1000 litres per hectare, instead of 10 lb. per acre in 100 gallons per acre. The results are given in Table 11 below.

TABLE 11

| No. of Compound (Table 1) | Pre-emergence | | | |
|---|---|---|---|---|
| | Lettuce | Tomato | Wheat | Maize |
| 26 | 3 | 3 | 1 | 0 |
| 27 | 3 | 3 | 0 | 0 |
| 28 | 3 | 3 | 3 | 0 |
| 29 | 3 | 3 | 3 | 0 |
| 32 | 3 | 3 | 3 | 1 |
| 34 | 3 | 2 | 3 | 3 |
| 38 | 3 | 3 | 2 | 0 |
| 40 | 3 | 3 | 1 | 1 |
| 42 | 3 | 3 | 3 | 3 |
| 43 | 3 | 1 | 1 | 0 |
| 44 | 2 | 3 | 3 | 0 |
| | Post-emergence | | | |
| 26 | 3 | 0 | 0 | 0 |
| 27 | 3 | 1 | 0 | 0 |
| 28 | 3 | 3 | 1 | 0 |
| 29 | 0 | 0 | 0 | 0 |
| 32 | 3 | 3 | 0 | 0 |

TABLE 11-continued

| | | | | |
|---|---|---|---|---|
| 34 | 0 | 0 | 0 | 0 |
| 38 | 3 | 3 | 0 | 0 |
| 40 | 3 | 1 | 0 | 0 |
| 42 | 2 | 3 | 0 | 0 |
| 43 | 3 | 3 | 0 | 2 |
| 44 | 3 | 3 | 0 | 1 |

In a further test, spray compositions prepared as in Example 5 were sprayed on to a further group of plant species at various rates of application. In this test the damage to the plant species was assessed on a scale of 0 to 5 where 0 represents no effect and 5 represents complete kill. The results are given in Table 12 below.

TABLE 12

| Compound No. (Table 1) | Application rate, kg/hectare | Pre- or Post-emergence test | Plant species | | | | | | | |
|---|---|---|---|---|---|---|---|---|---|---|
| | | | Sb | Ka | Ca | Pea | On | Bar | Ri | Oat |
| 27 | 5 | Pre | 4 | 4 | 4 | 3 | 0 | 0 | 0 | 0 |
| 28 | 5 | Pre | 5 | 5 | 5 | 5 | 5 | 5 | 5 | 5 |
| | 5 | Post | 5 | 4 | 4 | 0 | 0 | 0 | 0 | 0 |
| | 1 | Pre | 5 | 4 | 4 | 5 | 5 | 4 | 4 | 4 |
| | 1 | Post | 5 | 5 | 3 | — | 3 | 1 | 0 | 2 |
| 32 | 5 | Pre | 5 | 5 | 5 | 5 | 5 | 4 | 5 | 4 |
| | 5 | Post | 5 | 4 | 4 | 2 | 0 | 1 | 0 | 0 |
| | 1 | Pre | 4 | 4 | 3 | 3 | — | 4 | 4 | 3 |
| | 1 | Post | 5 | 5 | 2 | 3 | 1 | 1 | 0 | 1 |
| 42 | 5 | Pre | 5 | 4 | 5 | 2 | 5 | 3 | 3 | 4 |
| | 5 | Post | 5 | 5 | 5 | 1 | — | 1 | 0 | 4 |
| 43 | 5 | Pre | 0 | 1 | 0 | 0 | 0 | 1 | 0 | 0 |
| | 5 | Post | 5 | 5 | 5 | 5 | — | 3 | 1 | 4 |

EXAMPLE 7

This Example illustrates the selective herbicidal activity of compounds No. 5 and 12 of Table 1. The compounds, formulated as in Example 5 were sprayed on to pots of soil previously sown with seeds of the plant species shown in Tables 13 and 14. The results for compound 5 are shown in Table 13. These results are assessments of the damage to the plants 28 days after treatment, on a scale of 0 to 10 where 0 is no effect and 10 is complete kill.

TABLE 13

| Compound No. (Table 1) | Rate of application kg/hectare | Wheat | Barley | Plant species Redshank | Annual Nettle | May Weed |
|---|---|---|---|---|---|---|
| 5 | 0.5 | 0 | 0 | 5 | 10 | 6 |
| | 4 | 0 | 0 | 10 | 10 | 10 |
| | | Chick Weed | Groundsel | Speed-well | White mustard | Wild oat |
| 5 | 0.5 | 8 | 4 | 10 | 0 | 0 |
| | 4 | 10 | 10 | 10 | 8.5 | 5.5 |

Table 14 gives the results for compound No. 12 of Table 1 The figures are assessments of damage to the plants 23 days after treatment, on a scale of 0 to 5 where 0 is no effect and 5 is complete kill

TABLE 14

| Compound No. (Table 1) | Rate of application kg/hectare | Plant species | | | |
|---|---|---|---|---|---|
| | | Wheat | Barley | Speedwell | Knotgrass |
| 12 | 2 | 0 | 1 | 0 | 4 |
| | | Redshank | Corn Marigold | | Mayweed |
| 12 | 2 | 5 | 3.5 | | 5 |

It will be seen from Tables 13 and 14 that compounds 5 and 12 caused damage to the broadleaved plants, while wheat and barley were undamaged.

The botanical names of the plants used were as follows:

| Common name | Botanical name |
|---|---|
| Annual Nettle | Urtica urens |
| Chickweed | Stellaria media |
| Corn marigold | Chrysanthemum segetum |
| Groundsel | Senecio vulgaris |
| Knotgrass | Polygonum aviculare |
| Mayweed | Tripleurospermum maritimum ssp. inodorum |
| Redshank | Polygonum persicaria |
| White mustard | Sinapis alba |
| Wild oat | Avenua fatua |
| Speedwell | Veronica spp |

EXAMPLE 8

This Example illustrates the preparation of 3,5-dichloro-2,6-difluoro-4(4-nitro-2-trifluoromethylanilinopyridine (compound No. 5 of Table 1).

Sodium hydride (2.4 g. of a 50% dispersion in oil) was washed with anhydroous petroleum ether, suspended in dry dimethylformamide (20 ml.) and cooled in ice. 2-Amino-5-nitrotrifluoromethylbenzene (5.15 g.) in dimethyl formamide (10 ml.) was added dropwise to the stirred suspension while the temperature was kept below 10°C. 3,5-dichlorotrifluoropyridine (5.05 g.) in dimethyl formamide (5 ml.) was then added dropwise, keeping the temperature below 10°C. The mixture was allowed to warm to room temperature and stirred for 3 hours, then poured into ice (200 g.) The mixture was acidified and extracted with ether (2 × 75 ml.) The ether extracts were washed with water (2 × 50 ml.) and dried over magnesium sulphate. The residue after removal of the ether was recrystallised three times from carbon tetrachloride, giving the product as a pale yellow solid (2.92 g.) of melting point 117°C.

EXAMPLE 9

This Example illustrates the preparation of 3,5-dichloro-2,6-difluoro-4(2,4-dinitroanilinopyridine (compound No. 1 of Table 1).

Sodium hydride (2.4 g. of a 50% dispersion in oil) was washed with anhydrous petroleum ether and suspended in dry dimethylformamide (15 ml.) kept under an atmosphere of dry nitrogen. 4-Amino-3,5-dichloro-2,6-difluoropyridine (4.9 g.) in dry dimethylformamide (20 ml.) was added dropwise to the suspension which was stirred and kept at less than 10°C. A solution of 1-chloro-2,4-dinitrobenzene (5.1g.) in dry dimethyl formamide (20 ml.) was then slowly added keeping the temperature below 10°C. with stirring. The mixture was stirred for 3 hours, poured on to ice (200 g.) and acidified. The mixture was extracted with ether and the ether extracts washed three times with water (3 × 50 ml.) The residue from evaporation of the ether extract was extracted with boiling cyclohexane. The residue was taken up again in ether, washed again with water (2 × 50 ml. and the ether solution dried and evaporated. The residue was combined with the residue obtained by evaporation of the cyclohexane extract and recrystallised from carbon tetrachloride giving a yellow product (3.2 g.) of melting point 116°C.

EXAMPLE 10

Following the method of Example 8 the following compounds listed in Table 1 were prepared from the reactants stated. The number given after each compound is its number in Table 1.

4-Anilino-3,5-dichloro-2,6-difluoropyridine (No.2) from 3,5-dichlorotrifluoropyridine and aniline.

3,5-Dichloro-2,6-difluoro-4(2,6-dichloroanilino)pyridine (No. 3) from 3,5-dichlorotrifluoropyridine and 2,6-dichloroaniline.

3,5-Dichloro-2,6-difluoro-4(p-fluoroanilino)pyridine (No. 4) from 3,5-dichloro-2,4,6-trifluoropyridine and p-fluoroanilino.

3,5-Dichloro-2,6-difluoro-4(2,4,6-trichloroanilino)-pyridine (No. 7) from 3,5-dichlorotrifluoropyridine and 2,4,6-trichloroaniline.

3,5-Dichloro-2,6-difluoro-4(pentachloroanilino)pyridine (No. 9) from 3,5-dichlorotrifluoropyridine and pentachloroaniline.

3,5-Dichloro-2,6-difluoro-4(pentafluoroanilino)pyridine (No. 10) from 3,5-dichlorotrifluoropyridine and pentafluoroaniline.

3,5-Dichloro-2,6-difluoro-4(2-nitroanilino)pyridine (No. 11) from 3,5-dichlorotrifluoropyridine and 2-nitroaniline.

3,5-Dichloro-2,6-difluoro-4(2-bromo-5-trifluoromethylanilino)pyridine (No. 13) from 3,5-dichlorotrifluoropyridine and 2-bromo-5-trifluoromethylaniline.

3,5-Dichloro-2,6-difluoro-4(4-nitroanilino)pyridine (No. 14) from 3,5-dichlorotrifluoropyridine and 4-nitroaniline.

3,5-Dichloro-2,6-difluoro-4(2-nitro-4-trifluoromethylanilino) pyridine (No. 16) from 3,5-dichlorotrifluoropyridine and 2-nitro-4-trifluoromethylaniline.

3,5-Dichloro-2,6-difluoro-4(3-trifluoromethylanilino)-pyridine (No. 17) from 3,5-dichlorotrifluoropyridine and 3-trifluoromethylaniline.

3,5-Dichloro-2,6-difluoro-4(4-methoxy-2-nitroanilino)pyridine (No. 18) from 3,5-dichloro-trifluoropyridine and 4-methoxy 2-nitroaniline.

4(4-Cyano-2,3,5,6-tetrafluoroanilino)-3,5-dichloro-2,6-difluoropyridine (No. 19) from 3,5-dichlorotrifluoropyridine and 4-cyano-2,3,5,6-tetrafluoroaniline.

3,5-Dichloro-2,6-difluoro-4(2,5-dichloro-4nitroanilino)pyridine (No. 24) from 3,5-dichloro trifluoropyridine and 2,5-dichloro-4-nitroaniline.

3,5-Dichloro-2,6-difluoro-4(2,6-dichloro-4-nitroanilino)pyridine (No. 27) from 3,5-dichlorotrifluoropyridine and 2,6-dichloro-4-nitroaniline.

4-(4-Nitro-2-trifluoromethylanilino)-tetrafluoropyridine (No. 28) from pentafluoropyridine and 4-nitro-2-trifluoromethylaniline.

3,5-Dichloro-2,6-difluoro-4(4-chloro-2,6-dinitroanilino)pyridine (No. 29) from 3,5-dichlorotrifluoropyridine and 4-chloro-2,6-dinitroaniline.

3,5-Dichlor-2,6-difluoro-4(2,5-dichlor-4-N,N-dimethylsulphamoylanilino)pyridine (No. 31) from 3,5-dichlorotrifluoropyridine and 2,5-dichloro-4-N,N-dimethylsulphamoylaniline.

3-Chloro-4(4-nitro-2-trifluoromethylanilino)-2,5,6-trifluoropyridine (No. 32) from 3-chlorotetrafluoropyridine and 4-nitro-2-trifluoromethylaniline.

3,5-Dichloro-2,6-difluoro-4(4-nitro-3-trifluoromethylanilino) pyridine (No. 36) from 3,5-dichlorotrifluoropyridine and 4-nitro-3-trifluoromethylaniline.

3-Chloro-4(2,4-dinitroanilino)-2,5,6-trifluoropyridine (No. 38) from 3-chlorotetrafluoropyridine and 2,4-dinitroaniline.

4(2-Bromo-4,6-dinitroanilino)-3,5-dichloro-2,6-difluoropyridine (No. 40) from 3,5-dichlorotrifluoropyridine and 2-bromo-4,6-dinitroaniline.

4(4-Nitro-2-trifluoromethylanilino)-tetrachloropyridine (No. 41) from pentachloropyridine and 4-nitro-2-trifluoromethylaniline.

2-Fluoro-(4-nitro-2-trifluoromethylanilino)3,5,6-trichlorpyridine (No. 44) from 2,4-difluorotrichloropyridine and 4-nitro-2-trifluoromethylaniline.

2-Fluoro-3,4,5-trichlor-2(4-nitro-2-trifluoromethylanilino) pyridine (No. 47) from 2,6-difluoro-3,4,5-trichloropyridine and 4-nitro-2-trifluoromethylaniline.

2-Fluoro-3,5,6-tribromo-4(4-nitro-2-trifluoromethylanilino) pyridine (No. 48) from 2,4-difluoro-3,5-6-tribromopyridine and 4-nitro-2-trifluoromethylaniline.

3,5-Dibromo-2,6-difluoro-4(4-nitro-2-trifluoromethyl anilino) pyridine (No. 49) from 3,5-dibromotrifluoropyridine and 4-nitro-2-trifluoromethylaniline.

3,5-Dichloro-2,6-difluoro-4(2-bromo-4-nitroanilino)-pyridine (No. 50) from 3,5-dichlorotrifluoropyridine and 2-bromo-4-nitroaniline.

3,5-Dichloro-2,6-difluoro-4(2-methyl-4-nitroanilino)-pyridine (No. 51) from 3,5-dichlorotrifluoropyridine and 2-methyl-4-nitroaniline.

The halogenated pyridines used in the preparation of the foregoing compounds have been described in the literature, except for the bromofluoro compounds. The bromofluoropyridines may be prepared by vapour phase bromination of appropriate fluoropyridines. Thus, 2-4-difluorotribromopyridine can be prepared by vapour phase bromination of 2,4-difluoropyridine and 3,5-dibromotrifluoropyridine by similar bromination of 2,4,6-trifluoropyridine.

Following the method of Example 9 the following compounds listed in Table 1 were prepared from the reactants stated:

3,5-Dichloro-2,6-difluoro-4(2,4-dinitro-5-fluoroanilino)pyridine (No. 6) from 4-amino-3,5-dichloro-2,6-difluoropyridine and 1,5-difluoro-2,4-dinitrobenzene.

Tetrachloro-4(2,4-dinitroanilino)pyridine (No. 8) from 4-aminotetrachloropyridine and 2,4-dinitrochlorobenzene.

3,5-Dichloro-2,6-difluoro-4(4-nitro 2,3,5,6-tetrafluoroanilino) pyridine (No. 12) from 4-amino-3,5-dichloro-2,6-difluoropyridine and pentafluoronitrobenzene.

4(2,4-Dinitroanilino)-tetrafluoropyridine (No. 15) from 4-aminotetrafluoropyridine and 2,4-dinitrochlorobenzene.

3,5-Dichloro-2,6-difluoro-4(1-heptafluoronaphthylamino)pyridine (No. 20) from 4-amino-3,5-dichloro-2,6-difluoropyridine and octafluoronaphthalene.

2-Fluoro-3,5-dichloro-6methoxy-4(4-cyano-2,3,5,6-tetrafluoroanilino)pyridine (No. 21) from 4-amino-3,5-dichloro-2-fluoro-6-methoxypyridine and pentafluoro-cyanobenzene.

3,5-Dichloro-2,6-difluoro-4(2,4,6-trinitroanilino)pyridine (No. 22) from 4-amino-3,5-dichloro-2,6-difluoropyridine and 2,4,6-trinitrochlorobenzene.

3,5-Dichloro-2,6-difluoro-4(2,4-dinitro-1-naphthylamino) pyridine (No. 25) from 4-amino-3,5-dichloro-2,6-difluoro pyridine and 2,4-dinitro-1-chloronaphthalene.

4(2-Cyano-4-nitroanilino)-3,5-dichloro-2,6-difluoropyridine (No. 26) from 4-amino-3,5-dichloro-2,6-difluoropyridine and 2-cyano-4-nitrochlorobenzene.

4(4-Bromo-2,3,5,6-tetrafluoroanilino)-3,5-dichloro-2,6-difluoropyridine (No. 30) from 4-amino-3,5-dichloro-2,6-difluoropyridine and pentafluorobromobenzene.

3,5-Dichloro-4(3,4-dicyano-2,5,6-trifluoroanilino) 2,6-difluoropyridine (No. 33) from 4-amino-3,5-dichloro-2,6-difluoropyridine and 1,2-dicyano-tetrafluorobenzene.

4(4-Cyano-2,6-dinitroanilino)-3,5-dichloro-2,6-difluoropyridine (No. 34) from 4-amino-3,5-dichloro-2,6-difluoropyridine and 4-cyano-2,6-dinitrochlorobenzene.

4(5-Fluoro-2,4-dinitroanilino)tetrachloropyridine (No. 35) from 4-aminotetrachloropyridine and 1,5-difluoro-2,4-dinitrobenzene.

Tetrafluoro-4(2,4,6-trinitroanilino)pyridine (No. 37) from 4-amino-tetrafluoropyridine and 2,4,6-trinitrochlorobenzene.

4(2,4-Dinitro-5-fluoranilino)tetrafluoropyridine (No. 39) from 4-aminotetrafluoropyridine and 1,3-difluoro-4,6-dinitrobenzene.

4(4-Cyano-2,3,5,6-tetrafluoroanilino)tetrachloropyridine (No. 42) from 4-aminotetrachloropyridine and pentafluorocyanobenzene.

3,5-Dichloro-2,6-difluoro-4(3,5-difluoro-2,4,6-trichloroanilino) pyridine (No. 43) from 4-amino-3,5-dichloro-2,6-difluoropyridine and 1,3,5-trichloro-2,4,6-trifluorobenzene.

EXAMPLE 11

This Example illustrates the preparation of compound 46 of Table 1, 3,5-Dichloro-4(4-cyano-2,3,5,6-tetrafluoroanilino)-2-fluoro-6-methoxypyridine (3.0g.) in ether (40 ml.) was treated with methyl isocyanate (0.7 g.) N-methylmorpholine (3 drops) was added and the solution was allowed to stand at room temperature for one week. The white solid which separated was recrystallised from methylene dichloride/petroleum ether (bp40° – 60°C.) to give the product (3.3 g.)

Compound No. 45 of Table 1 was prepared in a similar way using 3,5-dichloro-2,6-difluoro-4(4-nitro-tetrafluoroanilino) pyridine and methyl isocyanate.

EXAMPLE 12

This Example illustrates a composition according to invention which comprises a concentrate comprising a miscible oil which is readily convertible by dilution with water into a liquid preparation suitable for spraying purposes.

The concentrate has the following compositions:

|  | % wt. |
|---|---|
| Compound No. 1 of Table 1 | 25.0 |
| 'LUBROL' L (Alkylphenol/ethylene oxide condensate; 'Lubrol' is a Trade Mark) | 2.5 |
| Calcium dodecylbenzenesulphonate | 2.5 |
| 'AROMASOL' H (alkylbenzene solvent 'Aromasol' is a Trade Mark) | 70.0 |
|  | 100.0 |

EXAMPLE 13

This Example also illustrates a concentrate which is in the form of a miscible oil. The composition of this concentrate is as follows:

|  | % wt. |
|---|---|
| Compound No. 2 of Table 1 | 25.0 |
| 'LUBROL' L ('Lubrol' is a Trade Mark) | 4.0 |
| Calcium dodecylbenzenesulphonate | 6.0 |
| 'AROMASOL' H ('Aromasol' is a Trade Mark) | 65.0 |
|  | 100.0 |

EXAMPLE 14

This Example illustrates a wettable powder having the following composition:

|  | % wt. |
|---|---|
| Compound No. of Table 1 | 25.0 |
| Sodium silicate | 5.0 |
| Calcium lignosulphonate | 5.0 |
| China clay | 65.0 |
|  | 100.0 |

EXAMPLE 15

This Example illustrates an atomisable fluid comprising a mixture consisting of 25% by weight of the compound No. 4 of Table 1 and 75% by weight of xylene.

EXAMPLE 16

This Example illustrates a dusting powder which may be applied directly to plants or other surfaces and comprises 1% by weight of compound No. 5 of Table 1 and 99% by weight of talc.

EXAMPLE 17

25 Parts by weight of compound NO. 6 of Table 1, 65 parts by weight of xylene, and 10 parts of an alkyl aryl polyether alcohol 'Triton' X-100 ('Triton' is a Trade Mark) were mixed There was thus obtained an emulsifiable concentrate which can be mixed with water to produce an emulsion suitable for use in agricultural applications.

EXAMPLE 18

5 Parts by weight of compound No. 7 of Table 1 were thoroughly mixed with 95 parts by weight of talc. There was thus obtained a dusting powder.

EXAMPLE 19

10 Parts by weight of compound No. 19 of Table 1, 10 parts of an ethylene oxide octylphenol condensate ("Lissapol" NX; 'Lissapol' is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 20

This Example illustrates a concentrated liquid formulation in the form of an emulsion. The ingredients listed below were mixed together in the stated proportions and the whole stirred until the constituents were dissolved.

| | % wt. |
|---|---|
| Compound No. 1 of Table 1 | 20 |
| 'LUBROL' ('Lubrol' is a Trade Mark) | 17 |
| Calcium dodecylbenzenesulphonate | 3 |
| Ethylene dichloride | 45 |
| 'Aromasol' H ('Aromasol' is a Trade Mark) | 15 |
| | 100 |

EXAMPLE 21

The ingredients listed below were ground together in the proportions stated to produce a powdered mixture readily dispersible in liquids.

| | % wt. |
|---|---|
| Compound No. 1 of Table 1 | 50 |
| Dispersol T | 5 |
| China ciay | 45 |
| | 100 |

EXAMPLE 22

A composition in the form of grains radily dispersible in a liquid (for example water) was prepared by grinding together the first four of the ingredients listed below in the presence of water and then mixing in sodium acetate. The mixture was dried and passed through a British Standard mesh sieve, size 44-100 to obtain the desired size of grains.

| | % wt. |
|---|---|
| Compound No. 2 of Table 1 | 50 |
| Dispersol T | 12.5 |
| Goulac | 5 |
| Calcium dodecylbenzenesulphonate | 12.5 |
| Sodium acetate | 2.5 |
| | 100 |

EXAMPLE 23

A granular composition was prepared by dissolving the active ingredient in acetone, spraying the solution obtained onto granules of pumice and allowing the solvent to evaporate.

| | % wt. |
|---|---|
| Compound No. 2 of Table 1 | 5 |
| Pumice Granules | 95 |
| | 100 |

EXAMPLE 24

An aqueous dispersion formulation was prepared by mixing and grinding the ingredients recited below in the proportions stated.

| | % wt. |
|---|---|
| Compound No. 3 of Table 1 | 40 |
| Calcium lignosulphonate | 10 |
| Water | 50 |
| | 100 |

EXAMPLE 25

This Example illustrates the activity of compounds used as the active ingredients of compositions according to the invention against a variety of plant bacterial diseases and fungal post-harvest saprophytic diseases. In a test for such activity, 5 milligrams of the compound to be tested was dissolved or suspended in 10 ml. of acetone and enough of this solution or suspension was added to 18 ml. of nutrient agar (for the bacterial diseases) or 16 ml. of 2% malt agar (for the fungal diseases) to give a final concentration of 50 parts per million of the compound under test. A streptomycin preparation (2 ml. containing 100 units per ml.) was added to the malt agar to prevent bacterial contamination of the fungal tests.

The agar preparations were dried overnight in Petri dishes and inoculated the following morning with the bacterial or fungal diseases using a multipoint inoculator. The antibacterial activity was assessed after 5 days and the antifungal activity after 6 days. The results of the tests are set out in Table 16 (anti bacterial activity) and Table 17 (antifungal activity). The results are graded as in Example 1 above. The names of the disease organisms are indicated in Table 15

TABLE 15

| Bacterial Disease Organism | Code Table 16 | Fungal disease Organism | Code Table 17 |
|---|---|---|---|
| Agrobacterium tumifaciens | B1 | Nigrospora sphaerica | F1 |
| Corynebacterium michiganense | B2 | Phytophthora eitrophthora | F2 |
| Xanthomonas | | Alternaria | |

TABLE 15-continued

| malvacearum | B3 | citri | F3 |
| --- | --- | --- | --- |

| Bacterial Disease Organism | Code Table 15 | Fungal Disease Organism | Code Table 17 |
| --- | --- | --- | --- |
| Erwinia carotovora | B4 | Diplodia natalensis | F4 |
| Xanthomonas oryzae | B5 | Phomopsis citri | F5 |
| Pseudomonas syringae | B6 | Ceratosystis paradoxa | F6 |
| Streptomyces scabies | B7 | Gloeosporium musarum | F7 |
| Pseudomonas mors-prunorum | B8 | Penicillium digitatum | F8 |
| Pseudomonas phaseolicola | B9 | Phoma exigua | F9 |
| Erwinia amylovora | B10 | Botrytis tulipae | F10 |
| | | Botrodiplodia theobromae | F11 |
| | | Fusarium caeruleum | F12 |

TABLE 16

| Compound No. Table 1 | B1 | B2 | B3 | B4 | B5 | B6 | B7 | B8 | B9 | B10 |
| --- | --- | --- | --- | --- | --- | --- | --- | --- | --- | --- |
| 1 | 3 | 3 | 3 | 3 | 3 | 3 | 3 | 3 | 3 | 3 |
| 6 | 3 | 3 | 3 | 1 | 2 | 2 | 1 | 1 | 0 | 1 |
| 15 | 3 | 3 | 3 | 3 | 3 | 3 | 3 | 3 | 3 | 3 |
| 19 | 3 | 3 | 3 | 3 | 3 | 3 | 3 | 3 | 3 | 3 |
| 20 | 0 | 3 | 3 | 2 | 1 | 2 | 2 | 0 | 0 | 0 |
| 21 | 2 | 3 | 3 | 3 | 2 | 3 | 3 | 1 | 2 | 3 |
| 24 | 3 | 3 | 3 | 3 | 3 | 3 | 3 | 2 | 3 | 2 |
| 29 | 3 | 3 | 3 | 3 | 3 | 3 | 3 | 3 | 3 | 3 |
| 33 | 3 | 3 | 3 | 3 | 3 | 3 | 3 | 0 | 0 | 3 |
| 34 | 0 | 3 | 2 | 0 | 2 | 3 | 3 | 0 | 0 | 1 |
| 35 | 0 | 0 | 0 | 0 | 1 | 2 | 2 | 0 | 0 | 2 |
| 40 | 2 | 2 | 3 | 1 | 2 | 1 | 2 | 1 | 1 | 2 |
| 41 | 3 | 0 | 2 | 1 | 1 | 1 | 0 | 0 | 3 | 2 |
| 44 | 3 | 3 | 3 | 3 | 3 | 3 | 3 | 3 | 3 | 3 |

TABLE 17

| Compound No. Table 1 | F1 | F2 | F3 | F4 | F5 | F6 | F7 | F8 | F9 | F10 | F11 | F12 |
| --- | --- | --- | --- | --- | --- | --- | --- | --- | --- | --- | --- | --- |
| 1 | 3 | 3 | 3 | 3 | 3 | 3 | 3 | 3 | 3 | 3 | 3 | 3 |
| 19 | 3 | 3 | 3 | 3 | 3 | 3 | 3 | 3 | 3 | 3 | 3 | 3 |
| 24 | 3 | 3 | 3 | 3 | 3 | 3 | 3 | 3 | 3 | 3 | 3 | 3 |
| 29 | 3 | 3 | 3 | 3 | 3 | 3 | 3 | 3 | 3 | 3 | 3 | 3 |
| 33 | 3 | 3 | 3 | 3 | 3 | 3 | 3 | 3 | 3 | 3 | 3 | 3 |
| 34 | 3 | 3 | 3 | 3 | 3 | 3 | 3 | 2 | 3 | 3 | 3 | 3 |
| 40 | 3 | 3 | 3 | 3 | 3 | 3 | 3 | 0 | 3 | 3 | 3 | 0 |
| 41 | 3 | 3 | 3 | 3 | 3 | 3 | 3 | 3 | 3 | 3 | 3 | 3 |
| 44 | 3 | 3 | 3 | 3 | 3 | 3 | 3 | 3 | 3 | 3 | 3 | 3 |

TABLE 18

| Compound No. | Activity relative to lindane |
| --- | --- |
| 19 | 5 |
| 22 | 5 |
| 25 | 5 |
| 28 | 6 |
| 34 | 5 |
| 37 | 5 |

In a similar test conducted with larvae of the tick *Boophilus microplus* maintained upon filterpaper (without addition of horse serum), compound No. 28 was found to be 10 times more toxic than lindane towards this organism.

The following constitutes an explanation of the compositions or substances represented by the various Trade Marks and Trade Names referred to in the foregoing Examples.

LUBROL L is a condensate of 1 mole of nonyl phenol with 13 molar proportions of ethylene oxide.

AROMASOL H is a solvent mixture of alkylbenzenes.

DISPERSOL T is a mixture of sodium sulphate and a condensate of formaldehyde with the sodium salt of naphthalene sulphonic acid.

LUBROL APN 5 is a condensate of 1 mole of nonyl phenol with 5 1/2 moles of naphthalene oxide.

CELLOFAS B 600 is a sodium carboxymethyl cellulose thickener.

LISSAPOL NX is a condensate of 1 mole of nonyl phenol with 8 moles of ethylene oxide.

We claim:

1. An arylaminopyridine compound of the formula:

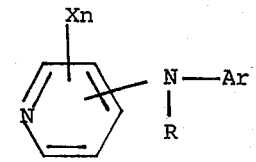

EXAMPLE 26

This Example illustrates the insecticidal activity of compounds used as active ingredients of the compositions of the invention. The compounds were submitted to a test in which a solution of the compound was applied to a filter paper upon which larvae of the blowfly (*Lucilia serrata*) were maintained. The filter paper upon which the blowfly larvae were kept was impregnated with horse serum. The toxic effects produced by the compounds used in the compositions of the invention were assessed by comparison with the effects of known insecticides. The results were expressed on a scale of 1 to 6 in which 5 represents insecticidal activity equal to that of the known insecticide and 6 represents activity 10 times that of the standard. The results are given below in Table 18.

or salt thereof wherein R represents hydrogen; Ar is phenyl or substituted phenyl bearing a substituent selected from the group consisting of chlorine, bromine, fluorine, nitro, cyano, alkyl of 1–4 carbon atoms and trifluoromethyl; X is selected from the group consisting of chlorine, bromine and fluorine; and $n$ is 3 or 4; provided that when X is Cl, and $n$ is 4, Ar is a substituted phenyl which bears 2 or 3 substituents.

2. A compound according to claim 1 wherein Ar is a substituted phenyl bearing a substituent as defined.

3. A compound according to claim 1 wherein $n$ is 4; X is chlorine or bromine; and the arylamino group

is in the 4-position.

4. A compound according to claim 1 wherein the arylamino group

is linked to the 4-position of the pyridine ring.

* * * * *